United States Patent
Dayton et al.

(10) Patent No.: US 12,349,941 B2
(45) Date of Patent: Jul. 8, 2025

(54) BONE POSITIONING AND CUTTING SYSTEM AND METHOD

(71) Applicant: Treace Medical Concepts, Inc., Ponte Vedra, FL (US)

(72) Inventors: Paul Dayton, Ankeny, IA (US); F. Barry Bays, Collierville, TN (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 18/615,875

(22) Filed: Mar. 25, 2024

(65) Prior Publication Data

US 2024/0260995 A1 Aug. 8, 2024

Related U.S. Application Data

(60) Continuation of application No. 17/503,730, filed on Oct. 18, 2021, now Pat. No. 11,937,849, which is a continuation of application No. 17/201,008, filed on Mar. 15, 2021, now Pat. No. 11,147,590, which is a continuation of application No. 16/730,424, filed on Dec. 30, 2019, now Pat. No. 10,945,764, which is a continuation of application No. 15/894,702, filed on (Continued)

(51) Int. Cl.
| | |
|---|---|
| *A61B 17/64* | (2006.01) |
| *A61B 17/15* | (2006.01) |
| *A61B 17/66* | (2006.01) |

(52) U.S. Cl.
CPC ........ *A61B 17/6416* (2013.01); *A61B 17/151* (2013.01); *A61B 17/66* (2013.01)

(58) Field of Classification Search
CPC . A61B 17/64; A61B 17/6416; A61B 17/6425; A61B 17/6458; A61B 17/66; A61B 17/7052; A61B 17/6441; A61B 17/645; A61B 17/6466; A61B 17/6491
USPC ...................................... 606/54–59, 90, 105
See application file for complete search history.

(56) References Cited

U.S. PATENT DOCUMENTS

| | | | |
|---|---|---|---|
| 3,664,022 A | 5/1972 | Small | |
| 4,069,824 A | 1/1978 | Weinstock | |

(Continued)

FOREIGN PATENT DOCUMENTS

| | | |
|---|---|---|
| AU | 2009227957 B2 | 7/2014 |
| CA | 2491824 A1 | 9/2005 |

(Continued)

OTHER PUBLICATIONS

"Accu-Cut Osteotomy Guide System," BioPro, Brochure, Oct. 2018, 2 pages.

(Continued)

*Primary Examiner* — Eduardo C Robert
*Assistant Examiner* — Christina Negrellirodriguez
(74) *Attorney, Agent, or Firm* — Fredrikson & Byron, P.A.

(57) ABSTRACT

A bone positioning device can include a fixation pin for attachment to a first bone and a fixation pin for attachment to a second bone. A first block having an aperture can be included for slidably receiving a fixation pin, and a second block having an aperture can be included for slidably receiving a fixation pin. A multi-axis joint can connect the first block and the second block, where the multi-axis joint allows the first second blocks to move with respect to each other about more than one axis.

27 Claims, 11 Drawing Sheets

Related U.S. Application Data

Feb. 12, 2018, now Pat. No. 10,555,757, which is a division of application No. 14/799,981, filed on Jul. 15, 2015, now abandoned.

(60) Provisional application No. 62/024,546, filed on Jul. 15, 2014.

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,364,381 A | 12/1982 | Sher et al. |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A * | 1/1991 | Pennig .................. A61B 17/66 606/57 |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,097,647 B2 | 8/2006 | Segler et al. |
| 7,112,204 B2 | 9/2006 | Justin et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| D679,395 S | 4/2013 | Wright et al. |

(56) References Cited

U.S. PATENT DOCUMENTS

| | | |
|---|---|---|
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,523,870 B2 | 9/2013 | Green et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,011,507 B2 | 4/2015 | Schelling |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,522,023 B2 | 11/2016 | Haddad et al. |
| 9,750,538 B2 | 9/2017 | Soffiatti et al. |
| 9,785,747 B2 | 10/2017 | Geebelen |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,779,867 B2 | 9/2020 | Penzimer et al. |
| 11,304,705 B2 | 4/2022 | Fallin et al. |
| 2002/0058944 A1 | 5/2002 | Michelson |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde, Jr. |
| 2005/0273112 A1 | 12/2005 | McNamara |
| 2006/0036257 A1 | 2/2006 | Steffensmeier |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0112212 A1 | 4/2009 | Murray et al. |
| 2009/0118733 A1* | 5/2009 | Orsak ............... A61B 17/6475 606/329 |
| 2009/0198244 A1 | 8/2009 | Leibel |
| 2009/0198279 A1* | 8/2009 | Zhang ............... A61B 17/7023 606/301 |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0264149 A1 | 10/2011 | Pappalardo et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |

(56) References Cited

U.S. PATENT DOCUMENTS

| | | |
|---|---|---|
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0042598 A1 | 2/2017 | Santrock et al. |
| 2017/0042599 A1 | 2/2017 | Bays et al. |
| 2017/0056031 A1 | 3/2017 | Awtrey et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2018/0132868 A1 | 5/2018 | Dacosta et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 103735306 A | 4/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | S635739 A | 1/1988 |
| JP | H0531116 A | 2/1993 |
| JP | 2004174265 A | 6/2004 |

(56) References Cited

FOREIGN PATENT DOCUMENTS

| | | |
|---|---|---|
| JP | 2006158972 A | 6/2006 |
| JP | 4134243 B2 | 8/2008 |
| JP | 2008537498 A | 9/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.

Coetzee et al., "The Lapidus Procedure: A Prospective Cohort Outcome Study," Foot & Ankle International, vol. 25, No. 8, Aug. 2004, pp. 526-531.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
International Patent Application No. PCT/US2016/018484, International Search Report and Written Opinion mailed Jun. 30, 2016, 12 pages.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"Hat-Trick Lesser Toe Repair System," Smith & Nephew, Brochure, Aug. 2014, 12 pages.
"Hat-Trick Lesser Toe Repair System, Foot and Ankle Technique Guide, Metatarsal Shortening Osteotomy Surgical Technique," Smith & Nephew, 2014, 16 pages.

(56) References Cited

OTHER PUBLICATIONS

Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.

(56) References Cited

OTHER PUBLICATIONS

Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.

Fallin et al., US Provisional Application Entitled Indexed Tri-Planar Osteotomy Guide and Method, U.S. Appl. No. 62/118,378, filed Feb. 19, 2015, 62 pages.

Fishco, "A Straightforward Guide to The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Gerard et al., "The Modified Lapidus Procedure," Orthopedics, vol. 31, No. 3, Mar. 2008, 7 pages.

Giannoudis et al., "Hallux Valgus Correction," Practical Procedures in Elective Orthopaedic Surgery, Pelvis and Lower Extremity, Chapter 38, 2012, 22 pages.

Greiner, "The Jargon of Pedal Movements," Foot & Ankle International, vol. 28, No. 1, Jan. 2007, pp. 109-125.

Groves, "Functional Position Joint Sectioning: Pre-Load Method for Lapidus Arthrodesis," The Podiatry Institute, Update 2015, Chapter 6, 2015, pp. 23-29.

Hardy et al., "Observations on Hallux Valgus," The Journal of Bone and Joint Surgery, vol. 33B, No. 3, Aug. 1951, pp. 376-391.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Integra, "Integra Large Qwix Positioning and Fixation Screw, Surgical Technique," 2012, 16 pages.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Myerson, "Cuneiform-Metatarsal Arthrodesis," The Foot and Ankle, Chapter 9, 1997, pp. 107-117.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Schon et al., "Cuneiform-Metatarsal Arthrodesis for Hallux Valgus," The Foot and Ankle, Second Edition, Chapter 8, 2002, pp. 99-117.

Sokoloff, "Lapidus Procedure," Textbook of Bunion Surgery, Chapter 15, 1981, pp. 277-287.

Stamatis et al., "Mini Locking Plate as "Medial Buttress" for Oblique Osteotomy for Hallux Valgus," Foot & Ankle International, vol. 31, No. 10, Oct. 2010, pp. 920-922.

Stewart, "Use for BME Speed Nitinol Staple Fixation for the Lapidus Procedure," date unknown, 1 page.

Wukich et al., "Hypermobility of the First Tarsometatarsal Joint," Foot and Ankle Clinics, vol. 10, No. 1, Mar. 2005, pp. 157-166.

Dayton et al., "Biwinged Excision for Round Pedal Lesions," The Journal of Foot and Ankle Surgery, vol. 35, No. 3, 1996, pp. 244-249.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.

Dayton et al., "Use of the Z Osteotomy for Tailor Bunionectomy," The Journal of Foot and Ankle Surgery, vol. 42, No. 3, May/Jun. 2003, pp. 167-169.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Wienke et al., "Bone Stimulation For Nonunions: What the Evidence Reveals," Podiatry Today, vol. 24, No. 9, Sep. 2011, pp. 52-57.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Dayton et al., "A User-Friendly Method of Pin Site Management for External Fixators," Foot and Ankle Specialist, Sep. 16, 2011, 4 pages.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

(56) References Cited

OTHER PUBLICATIONS

Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.

Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of Star Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation of Metatarsal Fracture With Bone Plate in a Dromedary Heifer," Open Veterinary Journal, vol. 3, No. 1, 2013, pp. 17-20.

(56) References Cited

OTHER PUBLICATIONS

Sidekick Stealth Rearfoot Fixator, Wright Medical Technology, Surgical Technique, Dec. 2, 2013, 20 pages.

Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

"Smith & Nephew scores a Hat-Trick with its entry into the high-growth hammer toe repair market," Smith & Nephew, Jul. 31, 2014, 2 pages.

Stableloc External Fixation System, Acumed, Product Overview, Effective date Sep. 2015, 4 pages.

Stahl et al., "Derotation of Post-Traumatic Femoral Deformities by Closed Intramedullary Sawing," Injury, vol. 37, No. 2, Feb. 2006, pp. 145-151, (Abstract Only).

Talbot et al., "Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Tricot et al., "3D-corrective osteotomy using surgical guides for posttraumatic distal humeral deformity," Acta Orthopaedica Belgica, vol. 78, No. 4, 2012, pp. 538-542.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fußchirurgie Das V-tek-System," ABW Wissenschaftsverlag GmbH, 2009, 11 pages, including English Abstract.

Weber et al., "A Simple System for Navigation of Bone Alignment Osteotomies of The Tibia," International Congress Series, vol. 1268, Jan. 2004, pp. 608-613, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

\* cited by examiner

BONE POSITIONING AND CUTTING SYSTEM AND METHOD

RELATED APPLICATIONS

This application is a continuation application of U.S. patent application Ser. No. 17/503,730, filed Oct. 18, 2021, which is a continuation application of U.S. patent application Ser. No. 17/201,008, filed Mar. 15, 2021, issued as U.S. Pat. No. 11,147,590, on Oct. 19, 2021, which is a continuation application of U.S. patent application Ser. No. 16/730,424, filed Dec. 30, 2019, issued as U.S. Pat. No. 10,945,764, on Mar. 16, 2021, which is a continuation application of U.S. patent application Ser. No. 15/894,702, filed Feb. 12, 2018, issued as U.S. Pat. No. 10,555,757, on Feb. 11, 2020, which is a divisional application of U.S. patent application Ser. No. 14/799,981, filed Jul. 15, 2015, which claims priority to U.S. Provisional Application No. 62/024,546, filed Jul. 15, 2014. The entire contents of each of these applications are hereby incorporated by reference.

TECHNICAL FIELD

This disclosure generally relates to devices and methods for positioning and cutting bones.

BACKGROUND

In various surgical procedures, it can be necessary to cut one or more bones. Success of such surgical procedures may often times be a function of the accuracy of the cut(s) being made to the one or more bones. Accomplishing accurate cuts can be especially complicated where surgical procedures involve cutting one or more bones that are relatively small as compared to bones in other locations of a surgical patient's anatomy. Exemplary surgical procedures involving cuts to one or more relatively small bones can include surgical procedures involving a foot or hand. To help facilitate accurate cuts to one or more bones, it may be useful to position the one or more bones to be cut in a manner that is conducive to a particular cut.

SUMMARY

One embodiment includes a bone positioning device. The embodiment of the bone positioning device can include at least one fixation pin for attachment to a first bone and at least one fixation pin for attachment to a second bone. A first block having at least one aperture can be included for slidably receiving a fixation pin(s), and a second block having at least one aperture can be included for slidably receiving a fixation pin(s). A multi-axis joint can connect the first block and the second block, where the multi-axis joint allows the first and second blocks to move with respect to each other about more than one axis.

Another embodiment includes a method for fixing an orientation of a first bone with respect to a second bone. The embodiment of the method can include attaching at least one fixation pin to a first bone and attaching at least one fixation pin to a second bone. At least one fixation pin can be inserted within a respective aperture of a first block, and at least one fixation pin can be inserted within a respective aperture of a second block. The first block can be positioned along and about the fixation pin(s) and a set screw(s) can be actuated to fix a position of the first block along and about the fixation pin(s), and similarly the second block can be positioned along and about the fixation pin(s) and a set screw(s) can be actuated to fix a position of the second block along and about the fixation pin(s). The position of the first block can be adjusted with respect to the second block about at least a first axis and a second axis. A set screw can be actuated to fix a position about the first axis, and a set screw can be actuated to fix a position about the second axis.

A further embodiment includes a bone cutting guide. The embodiment of the bone cutting guide can include a plate defining a plane, a block having a guiding surface integral with or coupled to the plate, with the guiding surface being parallel to the plane and being spaced laterally therefrom. A handle can also be included extending from the plate.

BRIEF DESCRIPTION OF THE DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

Figure 1:
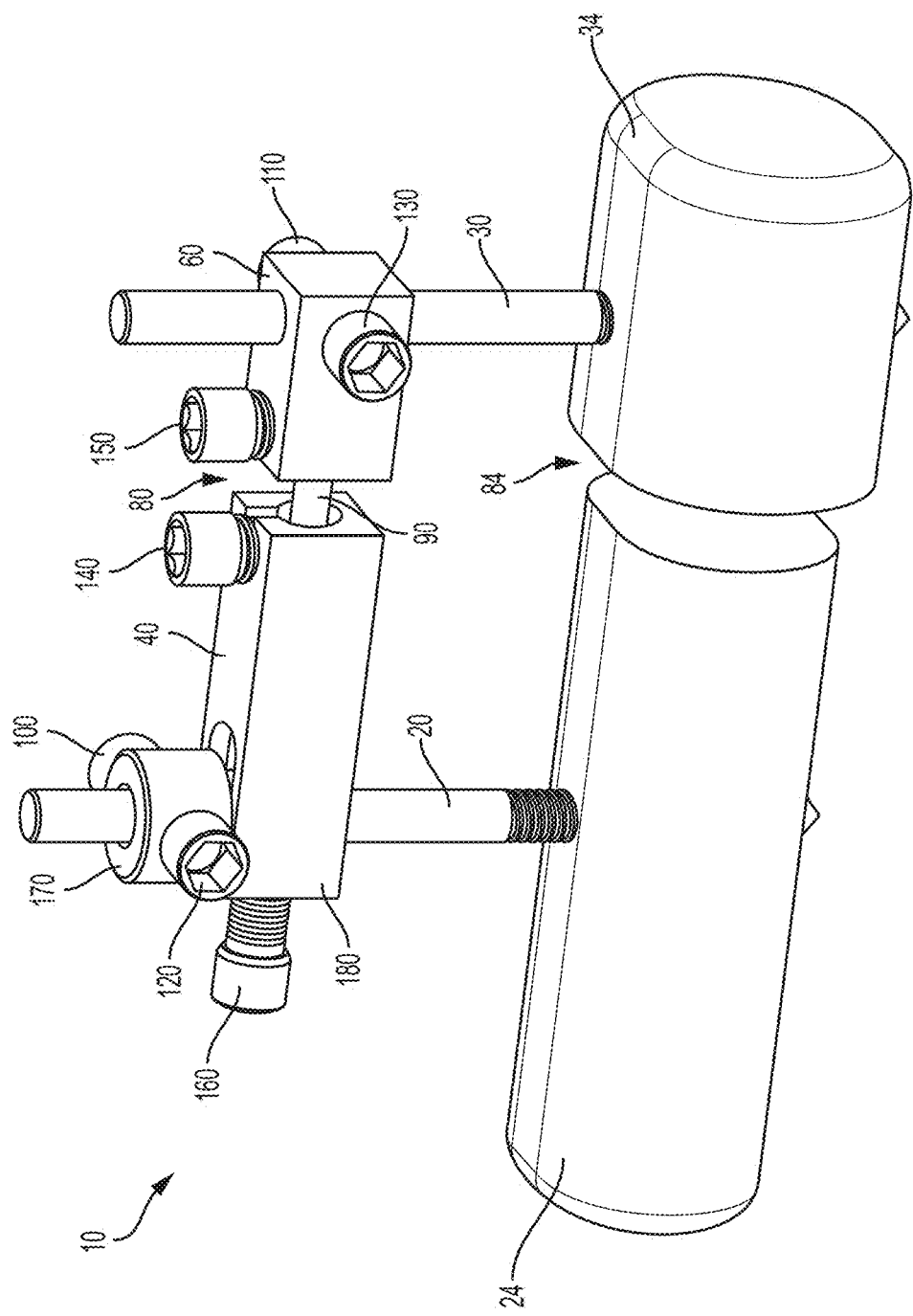
FIG. 1 is a perspective view of a bone positioning device according to an embodiment of the invention.

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention include a bone positioning device. Embodiments of the bone positioning device can be useful for temporarily fixing bones in a desired position during a surgical procedure, such as a bone alignment, osteotomy, and/or fusion procedure. Such a procedure may be performed, for example, on bones (e.g., adjacent bones separated by a joint or different portions of a single bone) in the foot or hand. In one example, the procedure can be performed to correct an alignment between a metatarsal (e.g. a first metatarsal) and a cuneiform (e.g., a first cuneiform), such as a bunion correction. An example of such a procedure is a Lapidus procedure. In another example, the procedure can be performed by modifying an alignment of a metatarsal (e.g. a first metatarsal). An example of such a procedure is a Basilar metatarsal osteotomy procedure.

As shown in FIGS. 1-4, the bone positioning device 10 can include at least one fixation pin, such as a first fixation pin 20, for attachment to a first bone 24. At least one fixation pin, such as a second fixation pin 30, can be provided for attachment to a second bone 34, such as an adjacent bone separated by a joint or different portions of a single bone. As shown best in FIG. 4, a first block 40 having a first aperture 50 can slidably receive the first fixation pin 20, and a second block 60 having a second aperture 70 can slidably receive the second fixation pin 30. The first and second apertures 50, 70 can allow the first and second blocks 40, 60 to slide along a longitudinal axis of the first and second fixation pins 20, 30, respectively. The first and second apertures 50, 70 can also allow the first and second blocks 40, 60 to rotate about the longitudinal axis of the first and second fixation pins 20, 30, respectively. In some embodiments, each of the first and second fixation pins 20, 30 are generally cylindrical and have a distal portion and a proximal portion, with the distal portion threaded for retention within the respective first or second bone, while the proximal portion is unthreaded for both sliding within the respective first or second aperture and free rotational movement within the respective first or second aperture. In some embodiments, the proximal portion has a uniform diameter, such that it does not contain a flared or "head" portion. In such embodiments, the first and second blocks can be positioned on the first and second fixation pins before or after the pins are engaged with bone.

Figure 4:
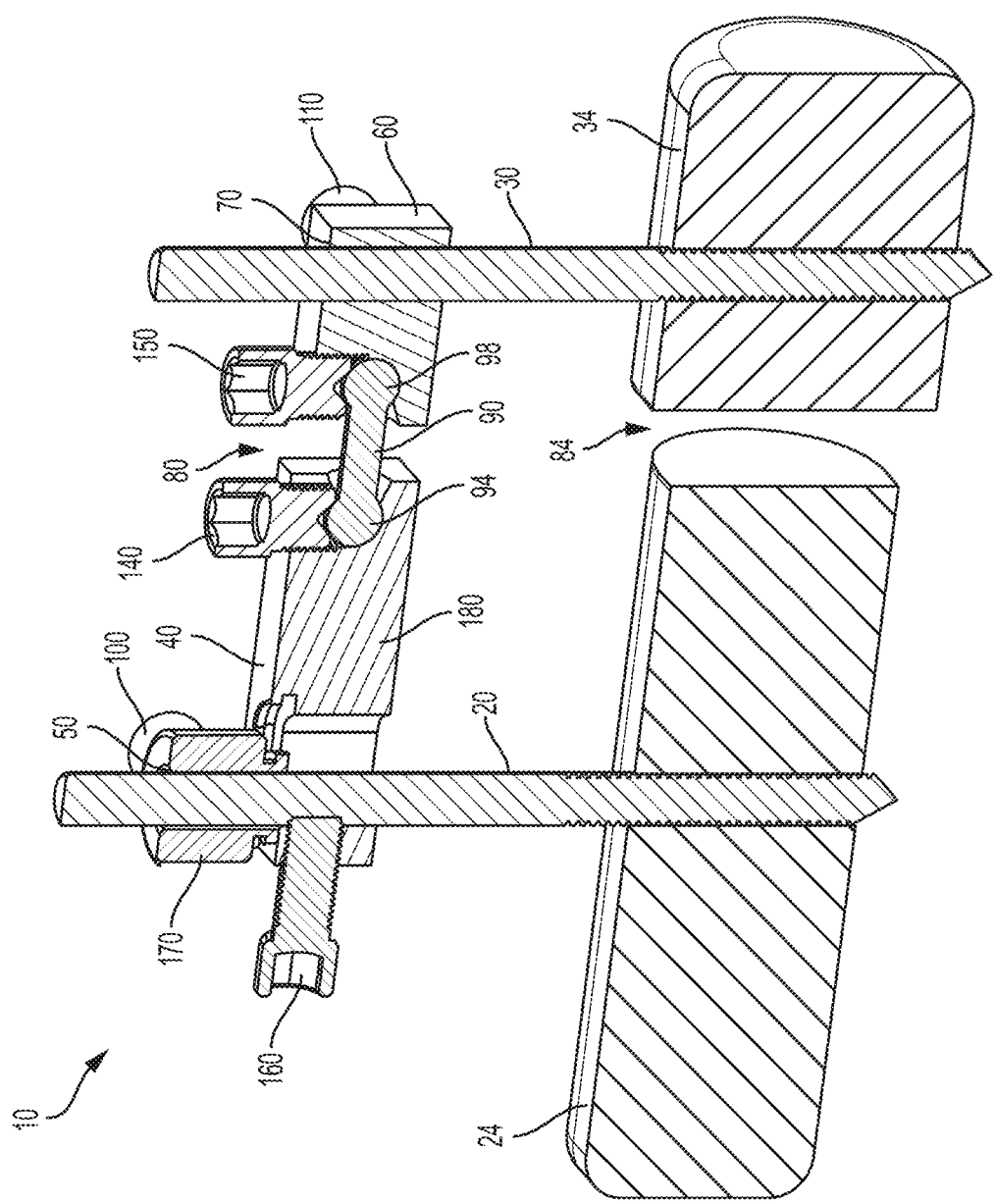
FIG. 4 is a perspective cross-sectional view of the bone positioning device of FIG. 1.
Figure 5:
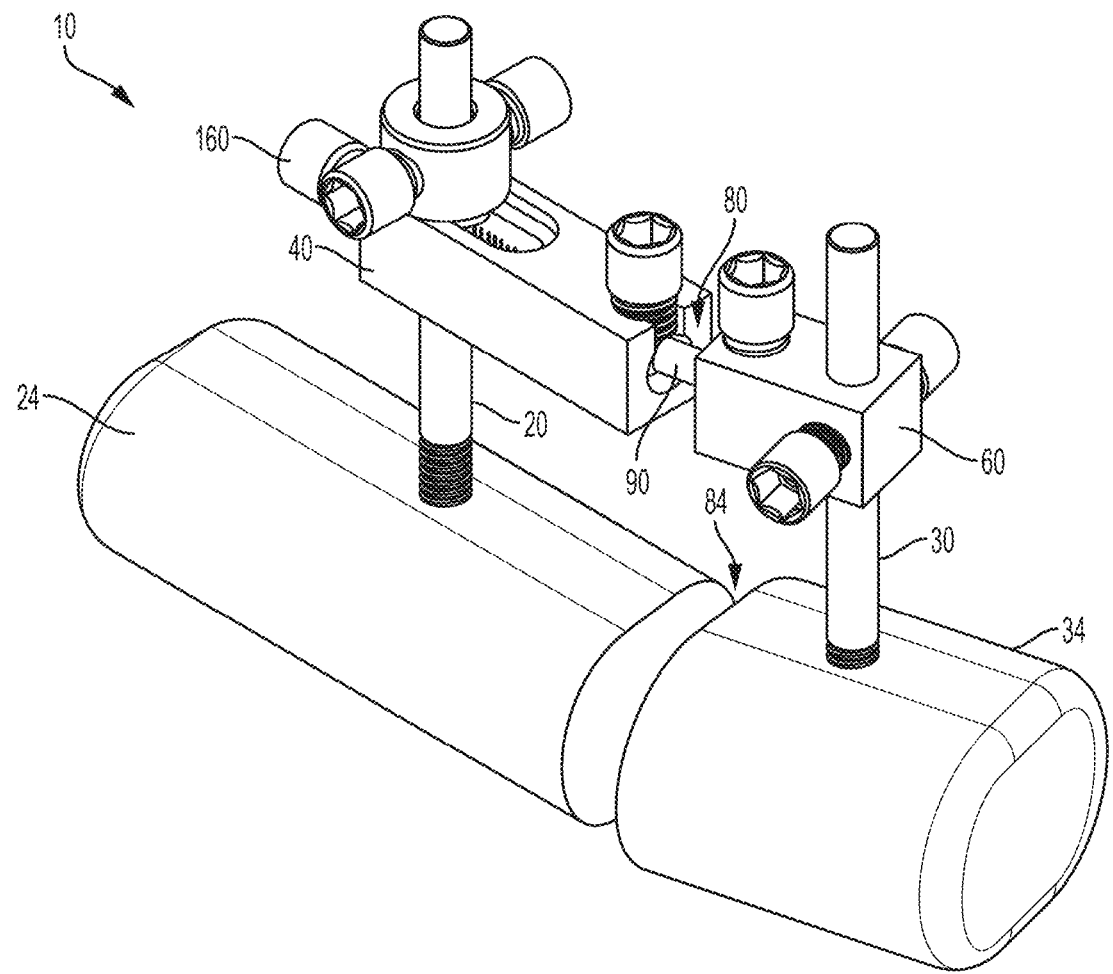
FIG. 5 is a perspective view of a bone positioning device attached to bones in a skewed position according to an embodiment of the invention.
Figure 6:
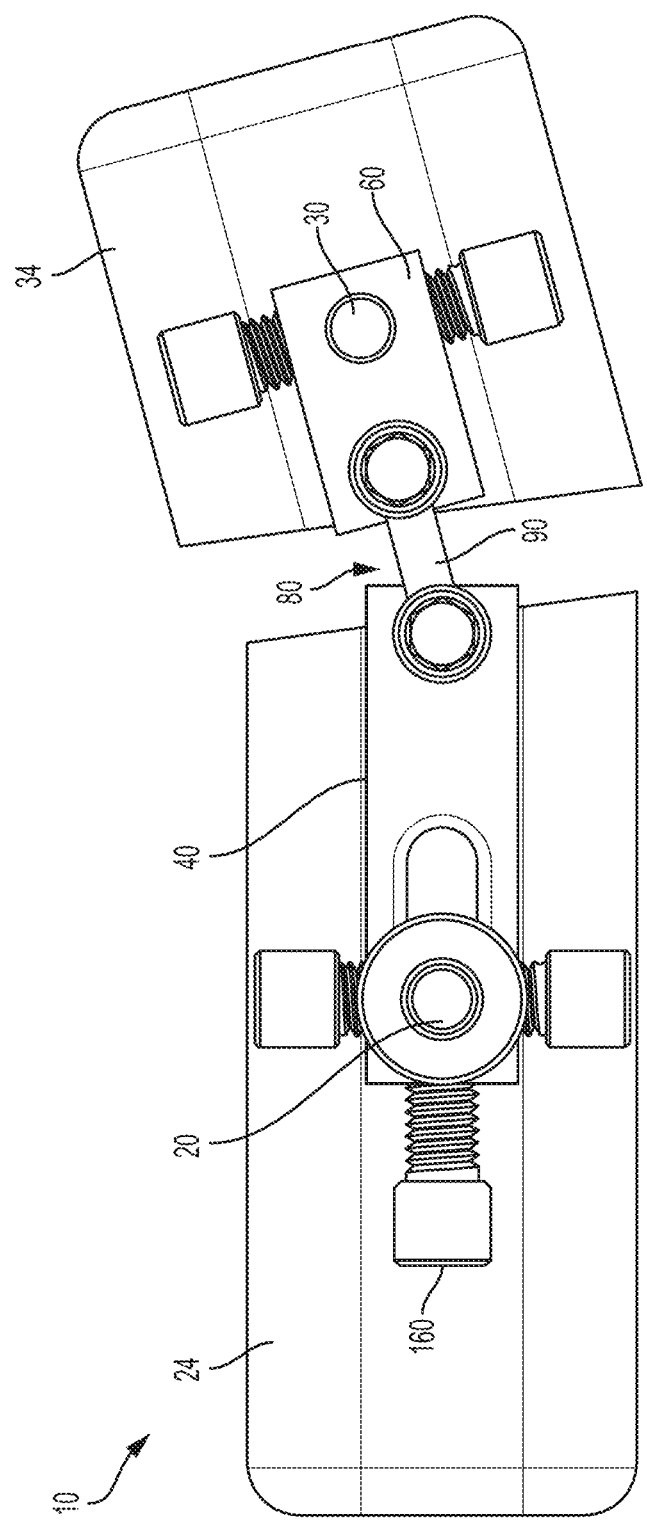
FIG. 6 is a top view of the bone positioning device of FIG. 5.
Figure 7:
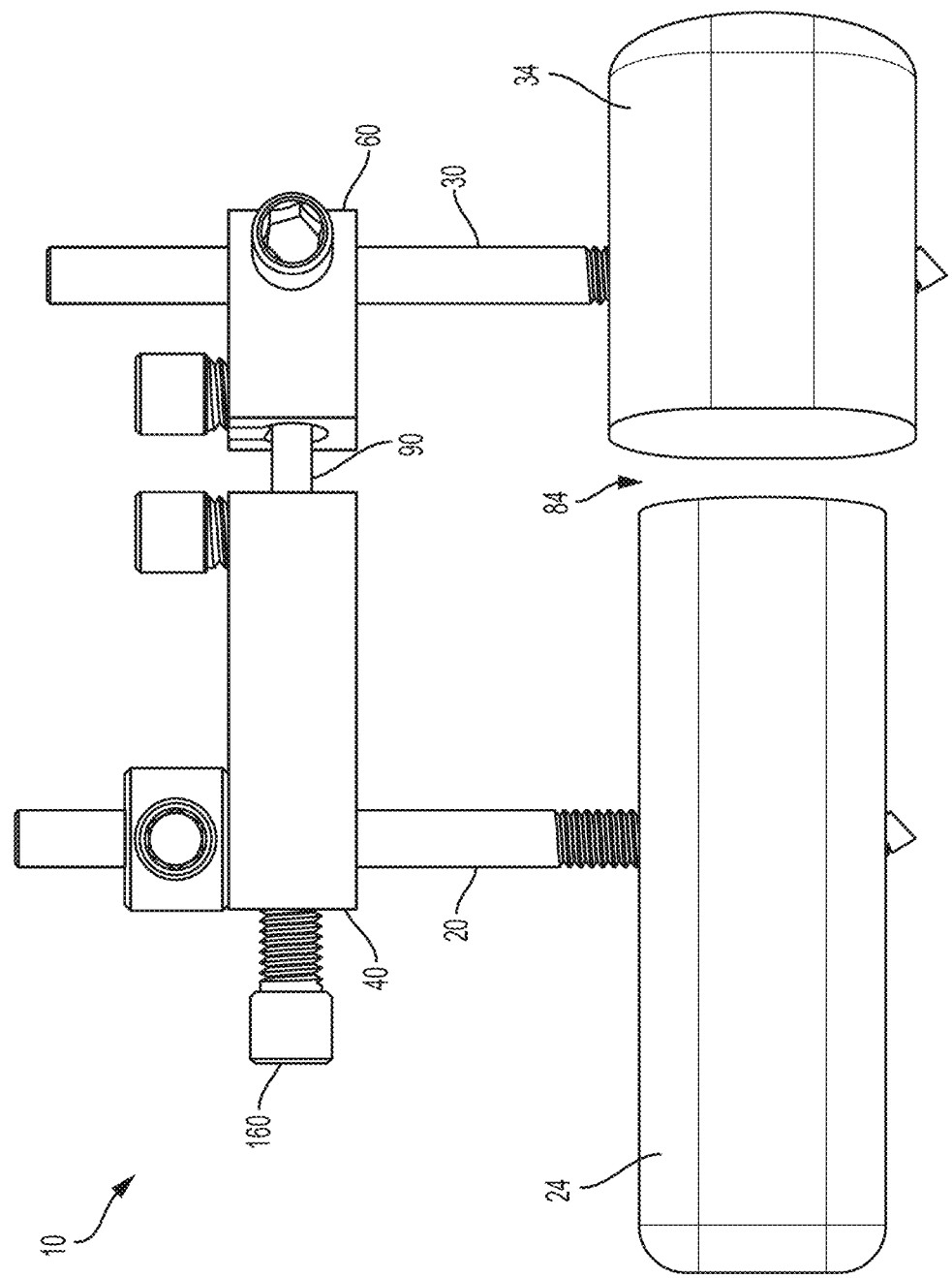
FIG. 7 is a side view of the bone positioning device of FIG. 5.
Figure 8:
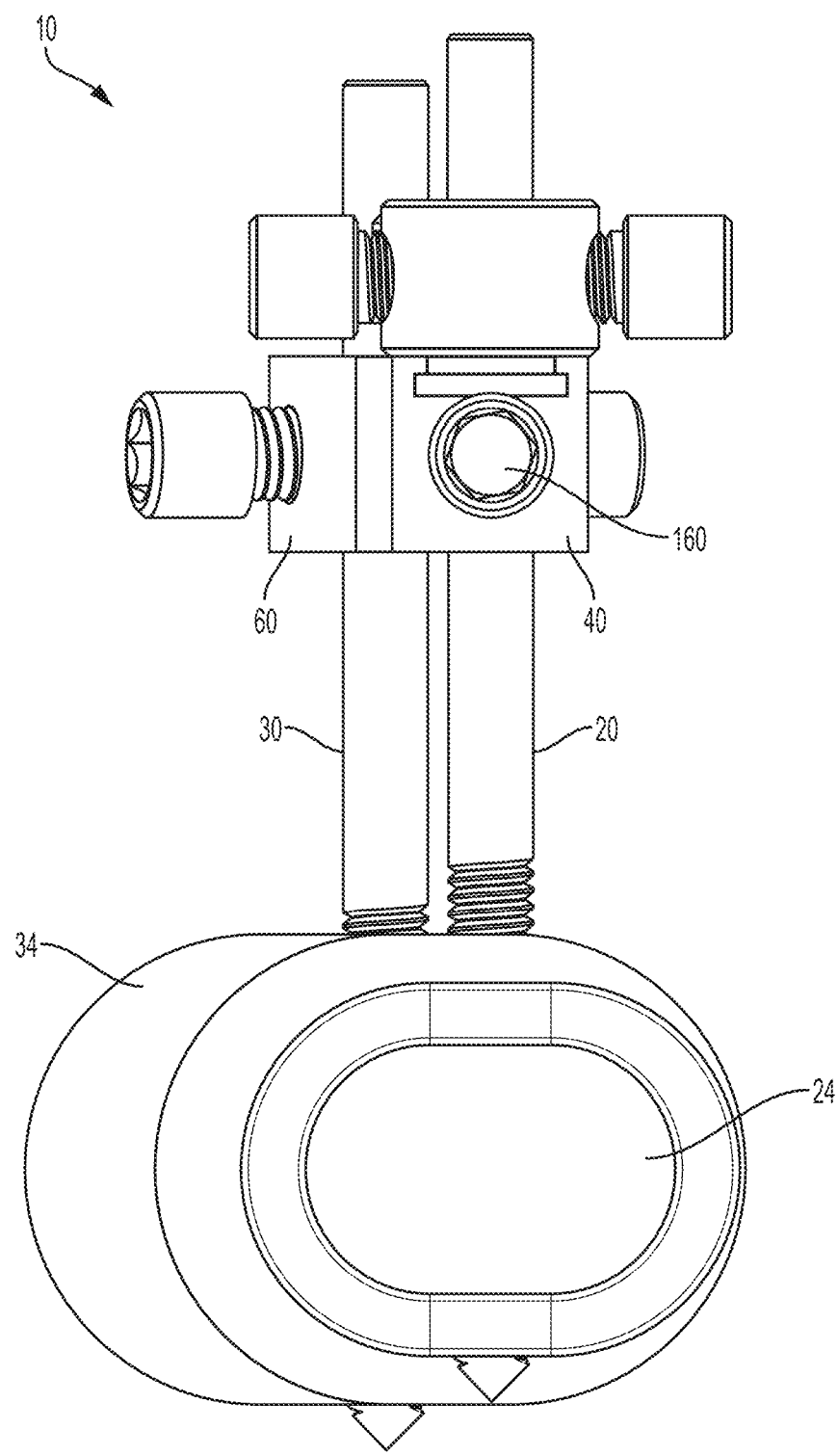
FIG. 8 is a side view of the bone positioning device of FIG. 5.

Again as shown best in FIG. 4, a multi-axis joint 80 can be provided to connect the first block 40 and the second block 60 and located adjacent to a joint 84 between the first and second bones. In some embodiments, the multi-axis joint 80 allows the first block 40 and the second block 60 to move with respect to each other about more than one axis. In certain embodiments, the multi-axis joint 80 allows the first block 40 and the second block 60 to move with respect to each other about the three cardinal planes (i.e., X, Y, and Z axes). In the embodiment shown, the multi-axis joint 80 allows for angulation in all directions and rotation between the first and second blocks. FIGS. 5-8 depict an exemplary embodiment of the bone positioning device 10 attached to first and second bones 24, 34, where the first and second bones are skewed relative to each other. In this particular embodiment, a longitudinal axis of second bone 34 is skewed about 15 degrees relative to a longitudinal axis of first bone 24.

The multi-axis joint can include any suitable structure for allowing desired adjustments about more than one axis, such as desired adjustments about three axes. In some embodiments, with reference to FIG. 4, the multi-axis joint 80 includes a link 90 having a first end 94 rotatably connected to the first block 40 and a second end 98 rotatably connected to the second block 60. Such a multi-axis joint allows for the movement about the various axes discussed above at both the first end and the second end. In the embodiment shown, the first end 94 includes a first ball received within a first socket of the first block 40, and the second end 98 includes a second ball received within a second socket of the second block 60.

Figure 2:
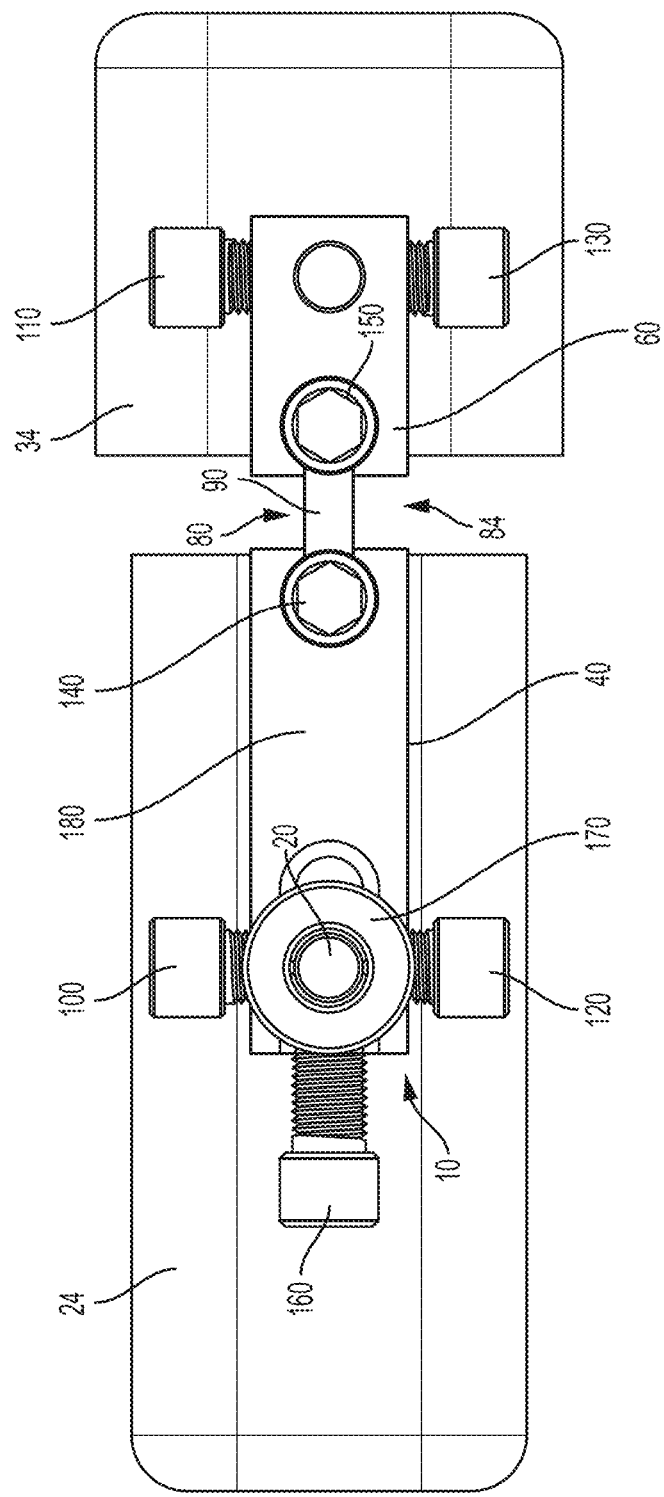
FIG. 2 is a top plan view of the bone positioning device of FIG. 1.
Figure 3:
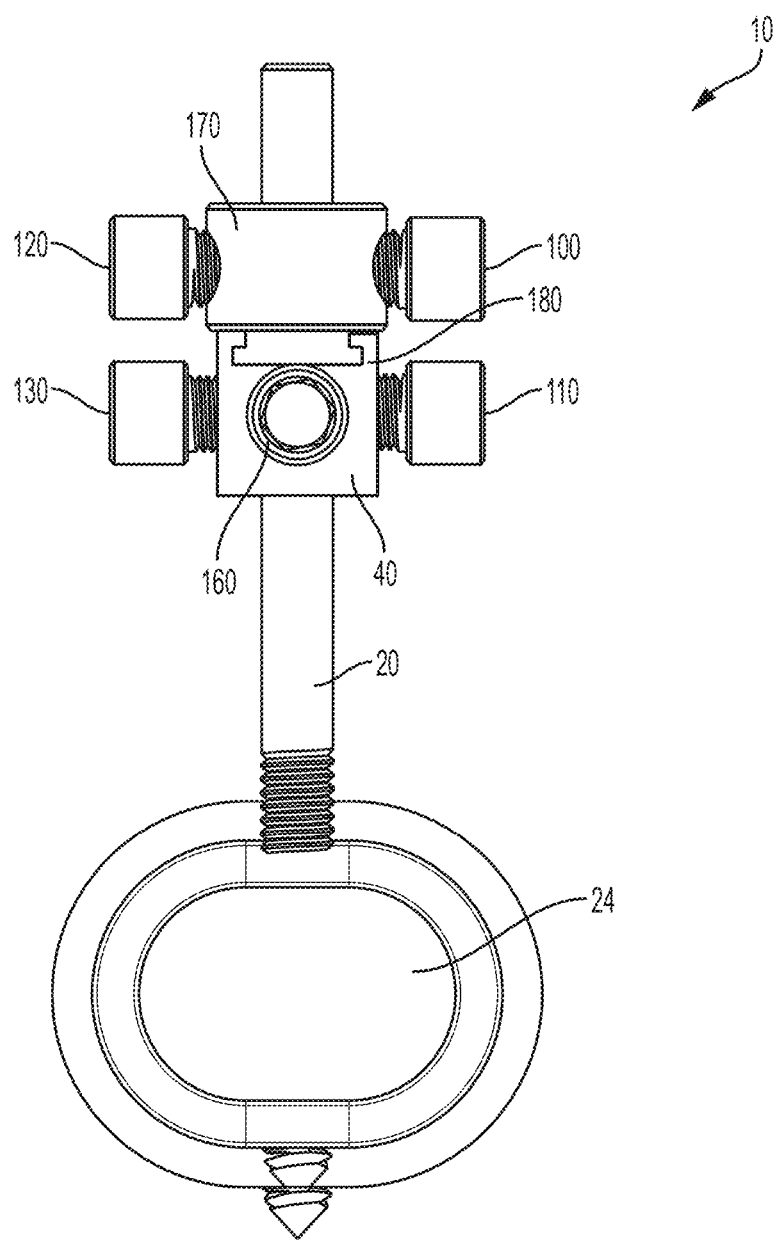
FIG. 3 is a side plan view of the bone positioning device of FIG. 1.

Some embodiments of the device allow the relative positions of the first and second bones to be fixed after a desired orientation has been achieved. For example, a first set screw 100 can extend through the first block 40 into the first aperture 50 and be positioned against the first fixation pin 20, for fixation of the first block on a longitudinal axis of the first fixation pin and/or about the longitudinal axis of the first fixation pin. Further, a second set screw 110 can extend through the second block 60 into the second aperture 70 and be positioned against the second fixation pin 30, for fixation of the second block on a longitudinal axis of the second fixation pin and/or about the longitudinal axis of the second fixation pin. In certain embodiments, the first and second set screws are positioned perpendicular to the first and second fixation pins. As shown in FIGS. 1-3, additional set screws 120, 130 extending through the first and second blocks can be positioned opposite of the first and second set screws, respectively. Such oppositely positioned set screws may facilitate use of the bone positioning device on a left foot or a right foot depending on a particular surgical procedure.

Set screws can also be provided to fix positions across the multi-axis joint. In the embodiment shown in FIG. 4, a first end set screw 140 extends through the first block 40 and is positioned against the first end 94 of the link 90. Further, a second end set screw 150 is shown extending through the second block 60 and positioned against the second end 98 of the link 90.

The set screws can include any structure suitable to fix the relative positions of the components described herein. In some embodiments, the set screws have a threaded connection with the blocks. Further, as shown, they can include a recess with a non-circular surface. Such a recess is useful for engagement with a driving tool, such as a hex-driver.

In some embodiments, the device can be used to apply a compression force between two adjacent bones, or different portions of a single bone, while the bones are held in desired alignment and/or to facilitate a desired alignment between the bones. Such a compression force is useful for certain surgical procedures, such as bone fusions. As shown in FIG. 4, in some embodiments the device 10 includes a compression screw 160 operable to exert a compression force between first and second bones 24, 34 connected to first and second fixation pins 20, 30, respectively. In the embodiment shown, the compression screw 160 is generally perpendicular to the fixation pins and is threadingly received within a block and positioned to act against one of the fixation pins.

One of the blocks can be adapted to allow for relative movement to exert the compression force. In the embodiment shown in FIG. 4, one of the blocks (e.g., the first block 40) has a first portion 170 slidingly connected to second portion 180. An aperture (e.g., the first aperture 50) extends through the first portion and the second portion. In this embodiment, the first aperture has a first cross-sectional area in the first portion and a second cross-sectional area in the second portion, and the first cross-sectional area is smaller than the second cross-sectional area. The set screw 100 can extend through the first portion 170. The compression screw 160 can extend through the second portion 180. Upon actuation, the compression screw 160 will act against the fixation pin 20 and will pull the second portion 180 of the block 40 away from the fixation pin 20. The force will be transmitted through the multi-axis joint 80 through the other block 60 and fixation pin 30, thereby applying a compression force that tends to press together leading surfaces (e.g., interfacing surfaces) of the first and second bones 24, 34.

Some embodiments include a bone cutting guide. Such a guide can be useful for guiding the cutting of bone, such as after a position of the bone has been fixed by the device described above. Bone cutting may be useful, for example, to facilitate contact between leading edges of adjacent bones or different portions of a single bone, such as in a bone alignment and/or fusion procedure.

Figure 9:
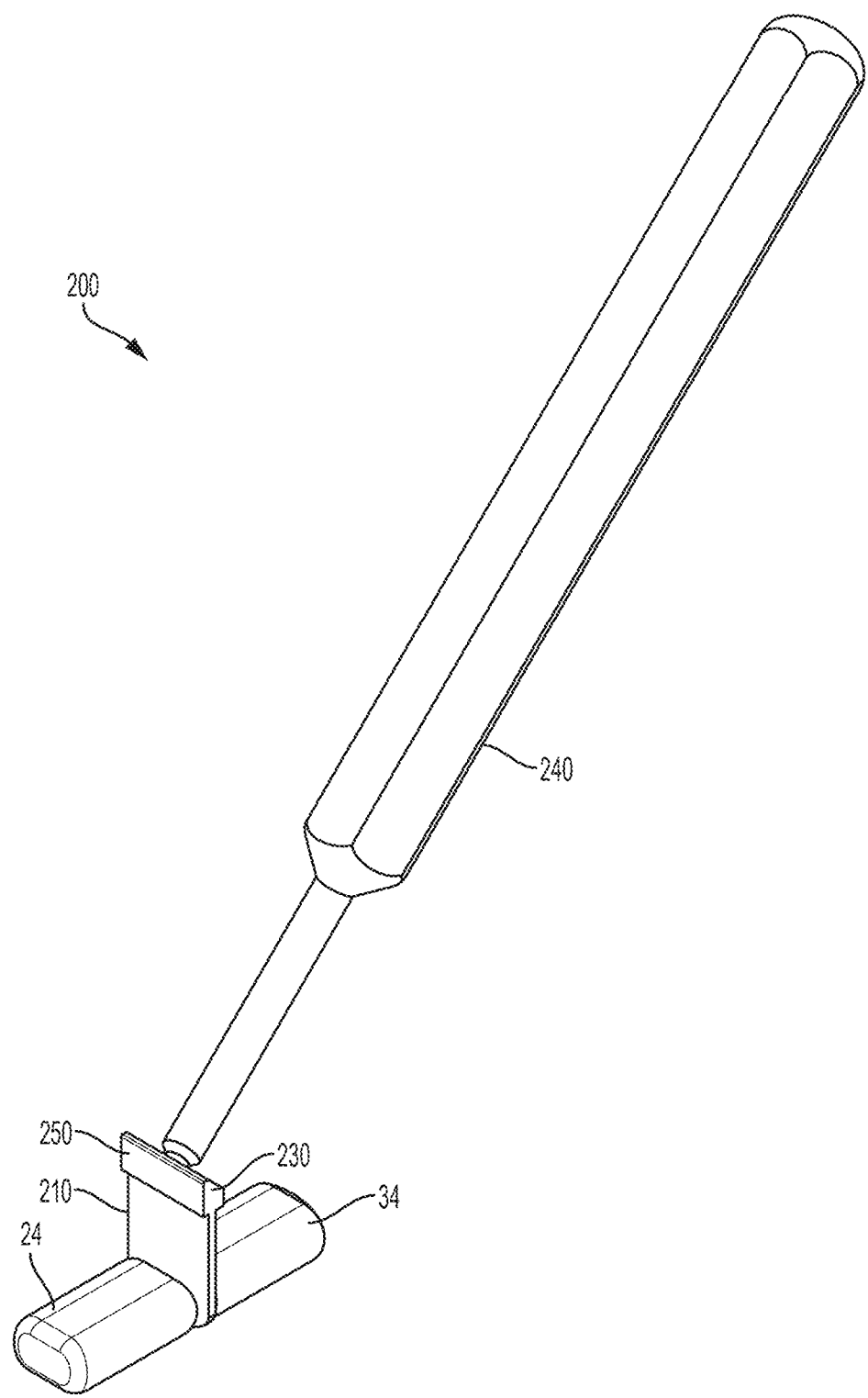
FIG. 9 is a perspective view of a bone cutting guide according to an embodiment of the invention.
Figure 10:
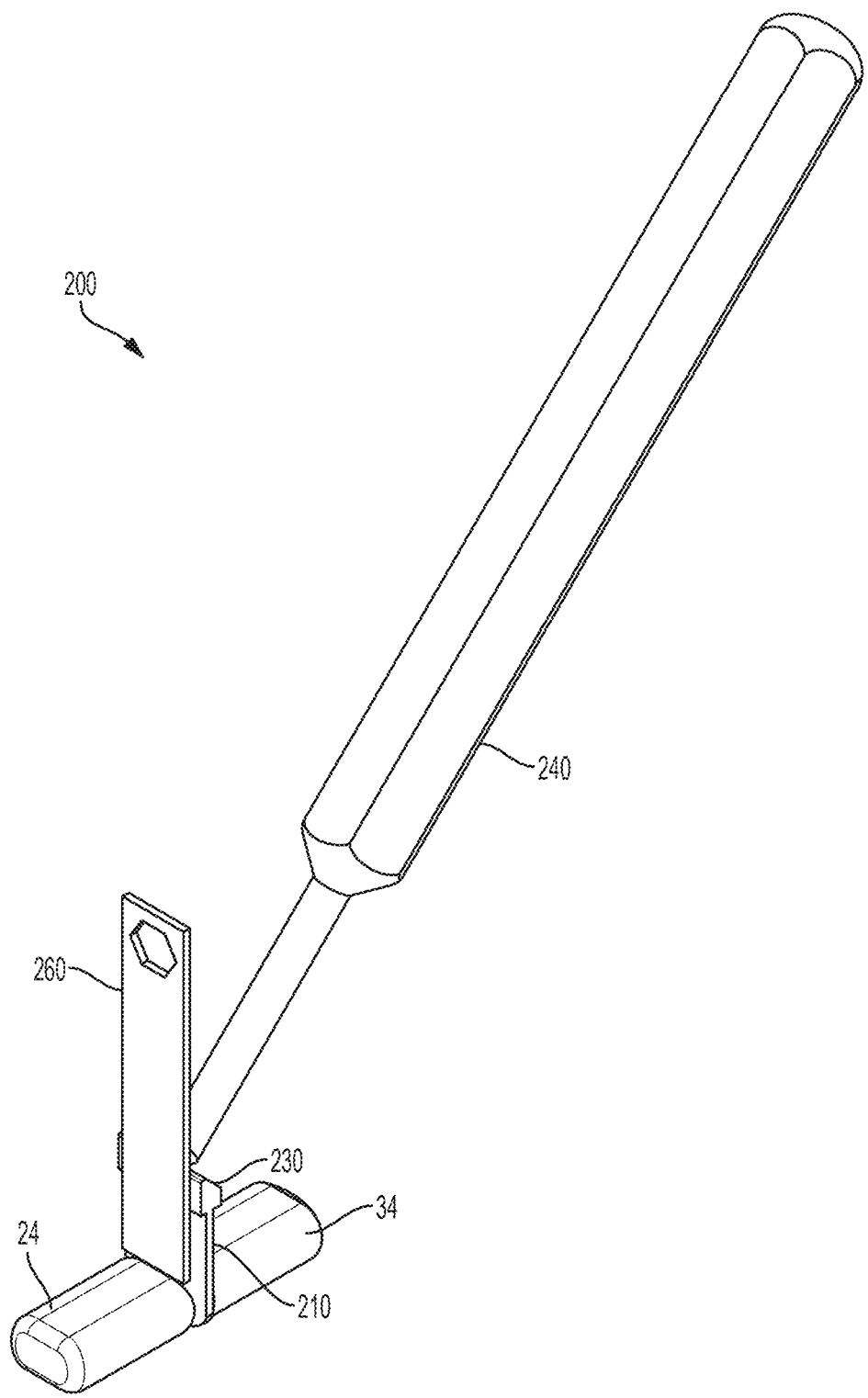
FIG. 10 is a perspective view of a bone cutting guide according to an embodiment of the invention in contact with a saw blade.
Figure 11:
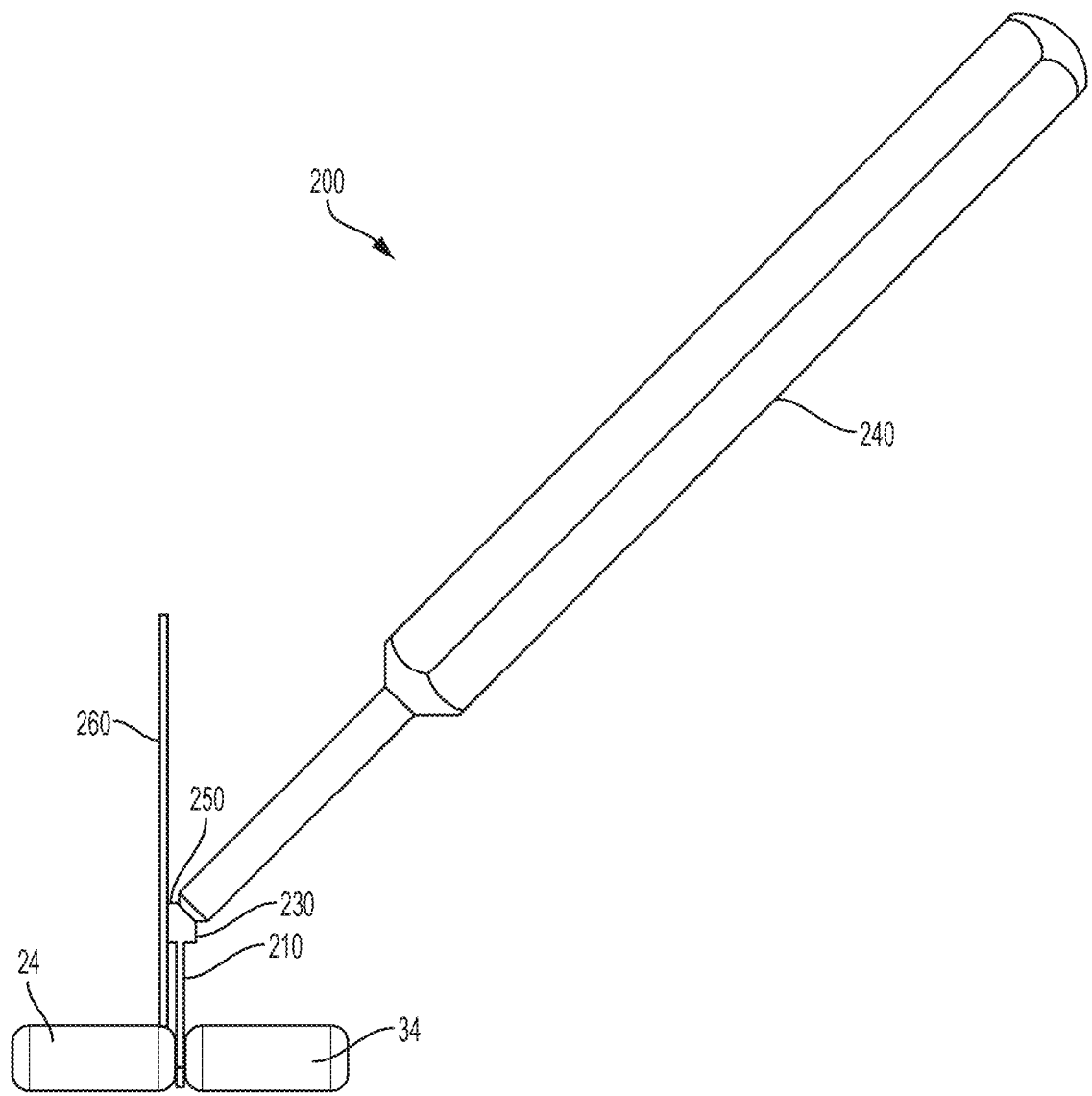
FIG. 11 is a side plan view of the bone cutting guide and saw blade of FIG. 10.

An embodiment of a bone cutting guide is shown in FIGS. 9-11. In the embodiment shown, the guide 200 includes a plate 210 that defines a plane, a block 230, and a handle 240 extending from the block 230. As shown, the handle extends from the block 230 at an angle of between 30 and 60 degrees (e.g., 45 degrees) with respect to the plane. The plate 210 can include a top edge, a bottom edge opposite of the top edge, and first and second opposite side surfaces. In the embodiment shown in FIG. 9, the block 230 can include a surface 250 parallel to the plate 210 and offset from the plate by a distance (e.g., 1-20 millimeters). As shown in FIGS. 10 and 11, a cutting tool 260, such as a saw blade, may be placed in apposition to the surface 250 to guide cutting in a plane parallel to the plate and offset from it by a distance (e.g., a distance the surface 250 if offset from the plate 210).

In use, the bottom edge of the plate 210 can be placed such that it extends into a joint space or resected portion between the first bone 24 and a second bone 34. The surface 250 can provide a cutting tool guide surface operable to guide a cutting tool to cut a leading edge of a bone in a plane parallel to the plate 210.

Embodiments of the invention also include methods of temporarily fixing the orientation of a first bone with respect to a second bone, such as during a surgical procedure, using a bone positioning device. In some embodiments, the method includes a step of attaching a first fixation pin slidably and rotatingly received within a first aperture of a first block to a first bone and attaching a second fixation pin slidably and rotatingly received within a second aperture of a second block to a second bone. The method can also include the steps of positioning the first block along the first fixation pin and actuating a first set screw to fix a position of the first block along the first fixation pin. Likewise, the method can include the steps of positioning the second block along the second fixation pin and actuating a second set screw to fix a position of the second block along the second fixation pin. In some embodiments, the method can include the steps of adjusting the position of the first block with respect to the second block about at least a first axis and a second axis and actuating a third set screw to fix a position about the first axis and actuating a fourth set screw to fix a position about the second axis. In certain embodiments, the method can also include actuating a compression screw to apply a compression force between the first and second bones. It should be noted these steps need not be performed in the order stated, which is merely exemplary. For example, the second fixation pin may be attached to the second bone before the first fixation pin is attached to the first bone, both fixation pins may be attached before either block is adjusted or fixed, etc.

The method may also include steps following the fixing of the position of the bones. Some embodiments of the method also include imaging (e.g., with an X-ray) the first and second bones connected to the first and second blocks to confirm a desirable alignment. Certain embodiments of the method include fusing the first bone and the second bone, such as by attaching a bone connector (e.g., a plate, pin, screw, wire, or staple) to stably connect and fix the first bone and the second bone. Some embodiments also include the step of removing the first fixation pin from the first bone and the second fixation pin from the second bone, such as at a time after the bones have been stabilized and connected with a bone connector.

Some embodiments of the method also include cutting a leading edge of the first or second bone using a cutting guide, such as by positioning a cutting guide proximate the bone (e.g., within a joint between adjacent bones or a resected portion of a single bone) and using the guide to cut a leading edge of the bone in a plane. Such embodiments can also include the step of actuating a compression screw to apply a compression force between the first and second bones after the cutting step.

Thus, embodiments of the invention are disclosed. Although the present invention has been described with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention.

What is claimed is:

1. A method of performing a bunion surgery to correct an alignment between a first metatarsal and a first cuneiform, the method comprising:
   engaging a bone positioning device with a first metatarsal using a first fixation pin and with a first cuneiform using a second fixation pin, the bone positioning device extending across a joint separating the first metatarsal from the first cuneiform;
   aligning a bone cutting guide with the joint between the first metatarsal and the first cuneiform, the bone cutting guide comprising a joint plate offset from a guide feature of the bone cutting guide, the joint plate extending downwardly relative to the guide feature, wherein aligning the bone cutting guide with the joint comprises inserting the joint plate into the joint;
   using the guide feature of the bone cutting guide to guide a cutting tool to cut a leading edge of the first metatarsal;
   using the bone positioning device to adjust an alignment of the first metatarsal in multiple planes to correct a bunion;
   compressing the first metatarsal and the first cuneiform together; and
   fixing a position of the first metatarsal relative to the first cuneiform with a bone connector.

2. The method of claim 1, further comprising, prior to fixing the position of the first metatarsal relative to the first cuneiform with the bone connector, temporarily fixing the position of the first metatarsal relative to the first cuneiform.

3. The method of claim 1, further comprising cutting a leading edge of the first cuneiform.

4. The method of claim 3, wherein cutting the leading edge of the first cuneiform comprises cutting the leading edge of the first cuneiform after using the bone positioning device to adjust the alignment of the first metatarsal.

5. The method of claim 3, wherein cutting the leading edge of the first cuneiform comprises using the guide feature of the bone cutting guide to guide the cutting tool to cut the leading edge of the first cuneiform.

6. The method of claim 1, further comprising, after fixing the position of the first metatarsal relative to the first cuneiform with the bone connector, removing the first fixation pin from the first metatarsal and removing the second fixation pin from the first cuneiform.

7. The method of claim 1, wherein the joint plate defines a plane, the guide feature defines a plane, and the plane defined by the joint plate is parallel to the plane defined by the guide feature.

8. The method of claim 7, wherein the bone cutting guide comprises a handle extending away from the joint plate at an angle between 30 degrees and 60 degrees with respect to the plane.

9. The method of claim 1, wherein the joint plate is offset from the guide feature by being spaced laterally from the guide feature, and the guide feature defines a guiding surface that is offset from the joint plate a distance ranging from 1 millimeter to 20 millimeters.

10. The method of claim 1, wherein the joint plate is integral with the guide feature.

11. The method of claim 1, wherein using the guide feature of the bone cutting guide to guide the cutting tool comprises placing the cutting tool in apposition to a guide surface defined by the guide feature of the bone cutting guide.

12. The method of claim 11, wherein the guide surface is operable to guide the cutting tool in a plane parallel to the guide surface.

13. The method of claim 1, wherein using the guide feature of the bone cutting guide to guide the cutting tool comprises placing the cutting tool in contact with a guide surface defined by the guide feature of the bone cutting guide.

14. The method of claim 1, wherein the cutting tool is a saw blade.

15. The method of claim 1, wherein the bone connector comprises one or more of a plate, a screw, and a pin.

16. The method of claim 1, wherein compressing the first metatarsal and the first cuneiform together comprises applying a force to press a first fixation pin inserted into the first metatarsal and a second fixation pin inserted into the first cuneiform toward one another.

17. The method of claim 1, wherein the bone positioning device comprises a sliding connection and a screw, and compressing the first metatarsal and the first cuneiform together comprises operating the screw.

18. A method of performing a bunion surgery to correct an alignment between a first metatarsal and a first cuneiform, the method comprising:

engaging a bone positioning device with a first metatarsal using a first fixation pin and with a first cuneiform using a second fixation pin, the bone positioning device extending across a joint separating the first metatarsal from the first cuneiform;

aligning a bone cutting guide with the joint between the first metatarsal and the first cuneiform, the bone cutting guide comprising a joint plate offset from a guide feature of the bone cutting guide, the joint plate extending downwardly relative to the guide feature, wherein aligning the bone cutting guide with the joint comprises inserting the joint plate into the joint;

using the guide feature of the bone cutting guide to guide a cutting tool to cut a leading edge of the first metatarsal;

using the bone positioning device to adjust an alignment of the first metatarsal in multiple planes to correct a bunion;

after using the bone positioning device to adjust the alignment of the first metatarsal in multiple planes to correct the bunion, cutting a leading edge of the first cuneiform;

compressing the first metatarsal and the first cuneiform together; and fixing a position of the first metatarsal relative to the first cuneiform with a bone connector.

19. The method of claim 18, further comprising, prior to fixing the position of the first metatarsal relative to the first cuneiform with the bone connector, temporarily fixing the position of the first metatarsal relative to the first cuneiform.

20. The method of claim 18, further comprising, after fixing the position of the first metatarsal relative to the first cuneiform with the bone connector, removing the first fixation pin from the first metatarsal and removing the second fixation pin from the first cuneiform.

21. The method of claim 18, wherein cutting the leading edge of the first cuneiform comprises using the guide feature of the bone cutting guide to guide the cutting tool to cut the leading edge of the first cuneiform.

22. The method of claim 18, wherein the joint plate defines a plane, the guide feature defines a plane, and the plane defined by the joint plate is parallel to the plane defined by the guide feature.

23. The method of claim 22, wherein the bone cutting guide comprises a handle extending away from the joint plate at an angle.

24. The method of claim 18, wherein the guide surface is operable to guide the cutting tool in a plane parallel to the guide surface.

25. The method of claim 18, wherein the bone connector comprises one or more of a plate, a screw, and a pin.

26. The method of claim 18, wherein compressing the first metatarsal and the first cuneiform together comprises applying a force to press the first fixation pin inserted into the first metatarsal and the second fixation pin inserted into the first cuneiform toward one another.

27. The method of claim 18, wherein the bone positioning device comprises a sliding connection and a screw, and compressing the first metatarsal and the first cuneiform together comprises operating the screw.

* * * * *